Feb. 11, 1975 R. KORDES Plant Pat. 3,685
ROSE PLANT
Filed Nov. 9, 1973
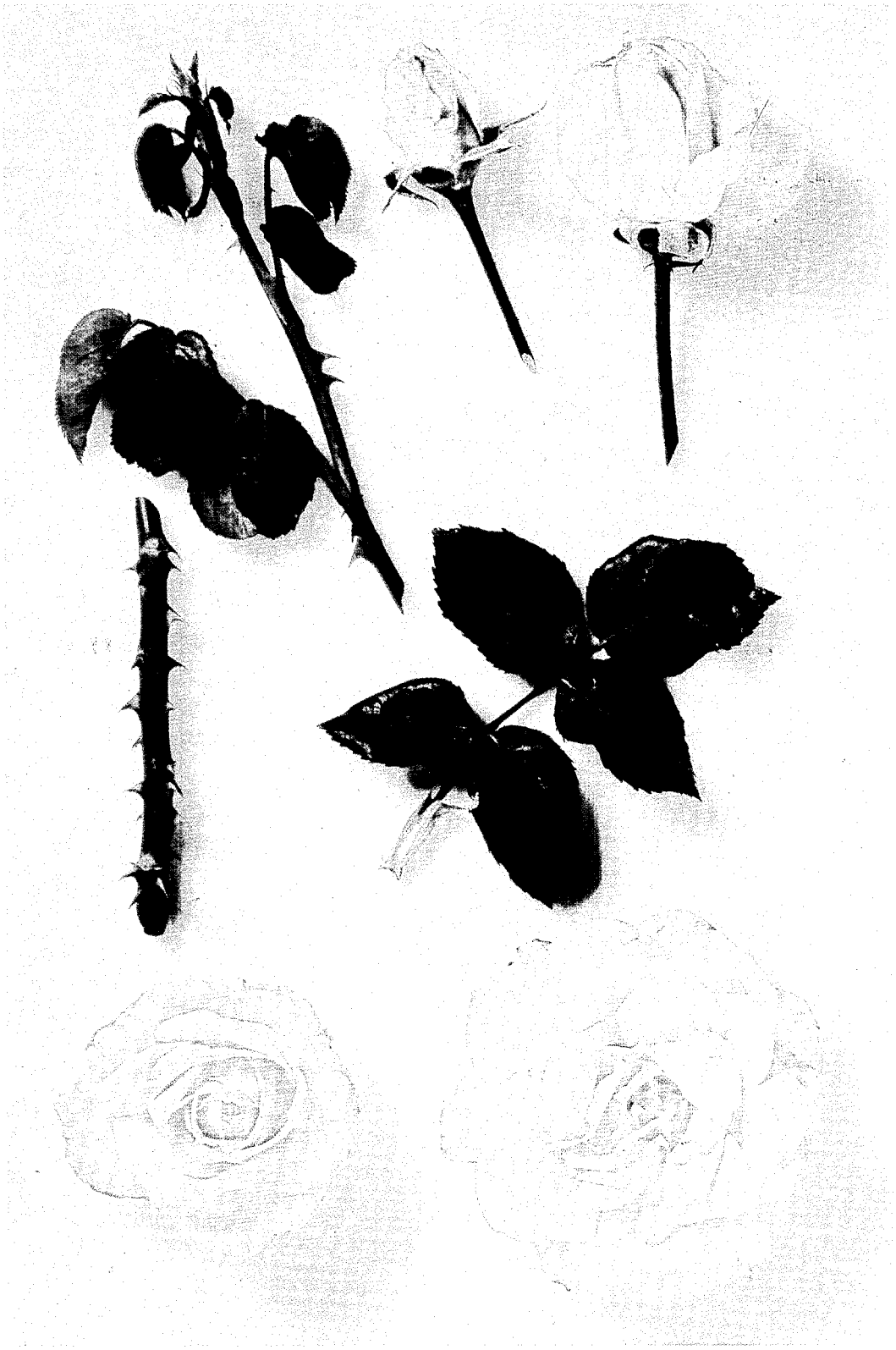

United States Patent

Plant Pat. 3,685

Patented Feb. 11, 1975

3,685

ROSE PLANT

Reimer Kordes, Sparrieshoop, near Elmshorn in Holstein, Germany, assignor to Jackson & Perkins Co., Medford, Oregon

Filed Nov. 9, 1973, Ser. No. 414,420

Int. Cl. A01h *5/00*

U.S. Cl.: Plt.—16 1 Claim

ABSTRACT OF THE DISCLOSURE

This present invention relates to a new and distinct cultivar of rose plant intermediate in classification between hybrid tea and floribunda which was originated by me by crossing the variety Konigin der Rosen and an unnamed seedling.

The primary objective of this breeding was to produce a new rose cultivar with blooms borne in abundance in large clusters but of the type usually associated with cultivars of the hybrid tea class. This objective was substantially achieved along with other desirable improvements as evidenced by the following unique combinations of characteristics which are outstanding in the new cultivar and which distinguish it from its parents as well as from all other cultivars of which I am aware:

1. A vigorous, heavily branched plant which grows in an upright manner.
2. A tendency for all large branches to terminate in floribunda type clusters of 10 or more flowers and smaller lateral branches to terminate in smaller clusters or occasionally single blooms.
3. Stems of flowers borne in clusters are long enough and strong enough to be used as cut flowers, i.e. they reach lengths of 8–12 inches, occasionally longer.
4. Bud color of a hue near Burnt Orange (014) with a large area of yellow near the petal base exposed as the buds open.
5. Opening flower color is lighter than Burnt Orange (014/3) but as the petals age, the color darkens to near Burnt Orange (014).
6. A very light fragrance.
7. Bud and flower size comparable to an average sized hybrid tea flower, reach an open flower size of four and one half inches.

Asexual reproduction of this new cultivar by budding as performed at Sparrieshoop, W. Germany and Wasco, Calif., shows that the foregoing characteristics and distinctions come true to form and are established and transmitted through succeding propagations.

The accompanying illustration shows typical specimens of the vegetative growth and flowers of this new cultivar in different stages of development, depicted in color as nearly true as it is reasonably possible to make the same in a color illustration of this character.

The following is a detailed description of my new rose variety with color terminology in accordance with *Wilson's Horticultural Color Chart,* except where ordinary dictionary significance of color is indicated.

Parentage:
- *Seed parent.*—Unnamed.
- *Pollen parent.*—Konigin der Rosen.

Classification:
- *Botanical.*—Rosa hybrid.
- *Commercial.*—Hybrid tea.

FLOWER

Observations were made at Irvine, Calif., in early August, from plants in a greenhouse.

Blooming habit: Recurrent—continuous.

Bud:
- *Size.*—Three quarters to one inch when petals start to unfurl.
- *Form.*—Pointed, ovoid.
- *Color.*—When sepals first divide—near Burnt Orange (014). When half blown; upper side of petals—near Burnt Orange (014/1) and (014/2); lower side of petals—Maize yellow (607) heavily overlaid with Burnt Orange (014/2)—The overlay effect is gradual from base to tip of petal such that near the base, the color is near Maize yellow (607) and at the tip the color is Burnt Orange (014/2).
- *Sepals.*—Color: Outer surface—Scheeles green (860/2) heavily overlaid with Garnet Brown (00918/3). Inner surface—heavy white tomentum. Three appendaged sepals normally appendaged. Two unappendaged sepals hairy edge.
- *Receptacle.*—Color: Scheeles green (860/2). Shape: Flat Funnel. Size: Broad. Surface: Smooth.
- *Peduncle.*—Length: Medium. Surface: Slightly prickly. Color: Slightly lighter than Garnet Brown (00918/3). Strength: Stiff, heavy.
- *Opening.*—Spiral with petals curling very little.

Bloom:
- *Size.*—Medium. Average size when fully expanded. three and one half to four inches.
- *Borne.*—Singly, in clusters. Clusters—flat.
- *Stems.*—Medium.
- *Form.*—When first open, high center. Permanence, retains its form to the end.
- *Petalage.*—Number of petals under normal conditions, 45–50.
- *Color.*—Center of flower: Upper side of petals—near Burnt Orange (014/2) with large area near base near Lemon yellow (4). Reverse side of petals—lighter than upper side, much lighter than Burnt Orange (014/3). Outer petals: Upper side of petals—same as center. Base of petals near Lemon yellow (4) on upper side and Maize yellow (607) on lower side. General tonality from a distance, near Burnt Orange (014/2). No variegations.
- *Discoloration.*—Color deepens with aging on hot days to near Poppy Red (16/1).
- *Fragrance.*—Slight.

Petals:
- *Texture.*—Thick.
- *Surface.*—Inside—satiny. Reverse—satiny.
- *Shape.*—Broad oval.
- *Form.*—Tips slightly recurved.
- *Arrangement.*—Imbricated.
- *Petaloids in center.*—Few.
- *Persistence.*—Drop off cleanly.
- *Lastingness.*—On the plant, long. As cut flower, long.

Reproductive parts:
- *Anthers.*—Large. Color, yellow. Arrangement, regular around styles.
- *Filaments.*—Medium and short. Color, mostly yellow.
- *Pollen.*—Gold yellow.
- *Styles.*—Loosely separated. Uneven color—reddish.
- *Stigmas.*—White.
- *Ovaries.*—All enclosed in calyx.

Fruit: Not observed.

Plant:
- *Form.*—Bush.
- *Growth.*—Vigorous, upright, branching. Main canes terminate in large flat clusters, secondary growth produces blooms singly and in small clusters. The plant has both floribunda and hybrid tea characteristics, but the latter predominate.

Foliage: Number of leaflets on normal mid-stem leaves, 5.

*Size.*—Medium.

*Quantity.*—Normal.

*Color.*—New foliage, slightly brighter than Garnet Brown (00918/3). Old foliage, deeper than Parsley Green (00962).

Leaflets:

*Shape.*—Oval pointed.

*Texture.*—Upper side-leathery. Under side-smooth. Ribs and veins-ordinary.

*Edge.*—Serrated.

*Serration.*—Single, small.

*Petiole.*—Rachis—color—green. Underside-prickles.

*Stipules.*—Long, bearded.

*Disease resistance.*—Moderately resistant to mildew under normal growing conditions at Irvine, Calif.

Wood:

*New wood.*—Color, Garnet Brown (00918/3).

*Bark.*—Smooth.

*Old wood.*—Color, green.

*Bark.*—Smooth.

Prickles:

*Quantity.*—On main stalks from base, ordinary. On laterals from stalks, ordinary.

*Form.*—Broad base, hooked downward.

*Color.*—When young, red to brown.

*Position.*—Irregular.

Small prickles:

*Quantity.*—On main stalks, few. On laterals, few.

*Color.*—Brown.

I claim:

1. A new and distinct cultivar of rose plant of a class intermediate between floribunda class and hybrid tea class, substantially as herein shown and described, characterized particularly as to novelty by the unique combinations of its heavily branched and clustering plant habit; hybrid tea type and size of flowers; medium sized and dark leathery foliage; Burnt Orange color of bud and open flower.

No references cited.

ROBERT E. BAGWILL, Primary Examiner